United States Patent
Berlien et al.

[11] Patent Number: 6,039,728
[45] Date of Patent: Mar. 21, 2000

[54] WORKING SHAFT FOR PHOTO-THERMAL THERAPY

[75] Inventors: Hans-Peter Berlien; Gerhard Muller; Jürgen Beuthan; Carsten Philipp, all of Berlin, Germany

[73] Assignees: Ceram Optec GmbH, Bonn; Huttinger Medizintechnik GmbH, Umkirch, both of Germany

[21] Appl. No.: 08/313,256

[22] PCT Filed: Apr. 2, 1993

[86] PCT No.: PCT/DE93/00321

§ 371 Date: Dec. 5, 1994

§ 102(e) Date: Dec. 5, 1994

[87] PCT Pub. No.: WO93/19680

PCT Pub. Date: Oct. 14, 1993

[30] Foreign Application Priority Data

Apr. 6, 1992 [DE] Germany ............................. 42 11 526
Oct. 30, 1992 [DE] Germany ............................. 42 37 286

[51] Int. Cl.[7] ....................................................... A61B 17/36
[52] U.S. Cl. ................................... 606/15; 606/17; 607/88
[58] Field of Search ................................. 606/15, 16, 17, 606/10, 11, 12; 607/88, 89

[56] References Cited

U.S. PATENT DOCUMENTS

| | | |
|---|---|---|
| 4,211,229 | 7/1980 | Wurster . |
| 4,273,109 | 6/1981 | Enderby . |
| 4,612,938 | 9/1986 | Dietrich et al. ........................... 606/15 |
| 4,718,417 | 1/1988 | Kittrell et al. . |
| 4,848,323 | 7/1989 | Marinjnissen et al. ...................... 128/6 |
| 4,986,628 | 1/1991 | Lozhenko et al. ...................... 350/96.1 |
| 5,054,867 | 10/1991 | Wagnières et al. . |
| 5,344,419 | 9/1994 | Spears ........................................ 606/15 |
| 5,415,655 | 5/1995 | Fuller et al. ............................... 606/16 |
| 5,429,635 | 7/1995 | Purcell, Jr. et al. ...................... 606/17 |

FOREIGN PATENT DOCUMENTS

| | | |
|---|---|---|
| 0101733 | 3/1984 | European Pat. Off. . |
| 0232511 | 8/1987 | European Pat. Off. . |
| 0 246 127 | 11/1987 | European Pat. Off. . |
| 0 255 974 | 2/1988 | European Pat. Off. . |
| 0362767 | 4/1990 | European Pat. Off. . |
| 0411132 | 2/1991 | European Pat. Off. ......... A61N 5/06 |
| 3323365 | 3/1984 | Germany . |
| 3532604A1 | 9/1984 | Germany . |
| 3512018 | 1/1987 | Germany . |
| 3813227 | 1/1989 | Germany . |
| 3833990 | 4/1990 | Germany . |
| 3833991 | 4/1990 | Germany . |
| 3901931 | 8/1990 | Germany . |
| 3941705A1 | 6/1991 | Germany . |
| 1405805 | 6/1988 | U.S.S.R. . |
| 1606128 | 11/1990 | U.S.S.R. . |

*Primary Examiner*—Linda C. M. Dvorak
*Assistant Examiner*—Sonya Harris-Ogugua
*Attorney, Agent, or Firm*—Bolesh J. Skutnik; B J Associates

[57] ABSTRACT

An optical working shaft system. The system includes a working shaft for insertion into a working tube of at least one of an endoscope and a catheter. The working shaft has a distal end defining a distal area in a vicinity thereof, and further includes: a device for radiating optical beams through the distal end; and a fluid for scattering the beams at least in the distal area. The fluid is operatively associated with the device for radiating such that, at least in the distal area, a path of the beams extends inside the fluid, the fluid further being effective as a coolant for removing waste heat generated by a scattering of the beams in the distal area.

28 Claims, 6 Drawing Sheets

WORKING SHAFT FOR PHOTO-THERMAL THERAPY

FIELD OF THE INVENTION

The invention relates to a working shaft for photo-thermal therapy as well as a device for executing the method of photo-thermal therapy.

BACKGROUND OF THE INVENTION

It is known from to transmit optical rays via optical fibers and catheter systems into the interior of a body, wherein the optical fibers are each provided with suitable scatter bodies.

Furthermore, a working shaft is known from DE-C-35 12 018, wherein a fluid is used for cooling and as the waveguide.

However, a number of grave problems arise when it is attempted to also use such systems in connection with endoscopic surgery or interventionally. In particular, impermissible heating occurs in the immediate vicinity of the distal end of the working shaft, which can constitute impermissible impairments.

Furthermore, the direction of the beam cannot be controlled and thus the effect cannot be visually observed simultaneously nor generally modified.

It is the object of the invention to provide the opportunity in connection with a working shaft of the type mentioned at the outset to apply a light beam to the interior of a body in a particularly simple manner in such a way that heating in the immediate area does not exceed impermissible values.

It should be possible in particular to affect the intensity and direction of thermal treatments over a wide range from outside of the body.

SUMMARY OF THE INVENTION

This object is attained by a working shaft system which includes a working shaft for insertion into a working tube of at least one of an endoscope and a catheter. The working shaft has a distal end defining a distal area in a vicinity thereof, and further includes: a device for radiating optical beams through the distal end; and a fluid for scattering the beams at least in the distal area. The fluid is operatively associated with the device for radiating such that, at least in the distal area, a path of the beams extends inside the fluid, the fluid further being effective as a coolant for removing waste heat generated by a scattering of the beams in the distal area.

The invention is based on the realization that the possibilities of use of photo-chemical and photo-thermal reactions, which can be triggered and controlled in the interior of the body in a simple manner by means of endoscopy and catheter systems which are today common in the market place, can be considerably improved if a fluid is provided between the area of emergence of the beam and, from an optical waveguide and a dome. The fluid is transparent to the beam, at the distal end of the working shaft, on the one hand, takes up the function of scattering the beam in the sense of evening the beam out in order to prevent too great a beam concentration in the impact area, and, on the other hand, makes possible local heat dissipation in the immediate vicinity of the distal end.

In the course of the above, it was further noted that at increasing distances, because of the non-linear removal of the heat generated by the beam, the removal of excess heat, which can lead to so-called "hot spots" and local carbonization of the tissue, by heat conduction alone was not sufficient in the immediate area of the distal end of the working shaft. Relief can only be obtained here by the possibility of improving the heat transport by circulating the cooling medium. The cooling effect is possibly further increased by means of a fluid which can be vaporized.

Normally the dimensions of the cross section of the working shaft are limited for reasons of insertability, so that therefore the center of the beam must also be concentrated in a relatively small area. However, with another advantageous further development of the invention the end area of the shaft is expandable, so that an increase in the surface of the area of emergence accessible to cooling can also be achieved.

In this way it is possible to remove the generated heat essentially directly in the area where it is created. Thus a non-directional diffuse illumination which, however, is homogenized, is present at the place of application, which can be arbitrarily concentrated in one or several predetermined spatial directions or deflected into these directions and can be produced by elements determining the direction of the beam—such as can be provided by a predetermined design of the emergence or reflection surfaces located in the area of the distal end. In the process it is possible in particular to transmit, at predetermined solid angles or directions, and isotropically, an optical beam in the wave length range between 400 nm to 1400 nm. The most diverse appropriate physical scattering mechanism in fluids are to be considered for the execution of the invention.

In the process it is possible in particular to create a device in the shape of a rigid or flexible working shaft for photo-thermal therapy, wherein an oil-water emulsion is washed into the radiation area of an optical fiber as the fluid scattering medium in order to isotropically scatter the laser beam emanating from the optical fiber. In this case it is also provided that this fluid scattering medium is precooled for compensating the temperature increases being created at the interface between the optical working shaft and the tissue to be irradiated. This way of proceeding is extremely advantageous for a plurality of uses.

In a preferred further development of the invention, a second optical shaft is pushed forward beyond the working tube of an endoscope, which at the distal end has a dome of a special shape sealed against fluids but optically transparent, wherein the shape in combination with the scattering properties of the dome materials is selected in such a way that predetermined volumetric elements can be sufficiently charged isotropically with optical radiation. In this connection it has been surprisingly shown that opalescent materials in crystal as well as glass form are particularly suited for light scattering, particularly when an ND:YAG or diode laser is employed.

In the process, the beam is preferably guided by an optical fiber waveguide to a proximal optical interface of the endoscope and inside the endoscope to the distal end by means of a suitable optical relay device. In a preferred way the optical relay device is designed in such a way that the distally attached light-scattering dome is illuminated as homogeneously as possible. In a further development of the concept of the invention, the energy-transferring optical fiber is also continued inside the endoscope shaft, depending on the size of the endoscope system, as far as the distally attached light-scattering dome. However, in accordance with the invention in this case the numerical aperture of the optical fiber must be adapted to the desired solid angle.

In a further development of the concept of the invention, the entire light-scattering tube inserted into the working tube of an endoscope is washed by a fluid to prevent heating of the applicator itself by vagrant stray light from the laser beam.

In another preferred embodiment a light-scattering fluid, such as an oil-water emulsion, which in the preferred exemplary embodiment is produced in an ultrasonic bath from silicon oil and water (mixed with suitable dispersants, if required), is also used as a cooling medium and is then coaxially directed through the endoscope shaft via a recirculating pump, wherein it is possible to adjust the scattering properties of the oil-water emulsion over a wide range by means of the frequency and intensity of the ultrasonic bath, so that it is possible in this manner to change the emission characteristics at the distal end of the optical scattering tube in a predeterminable way. In a further preferred embodiment a flexible catheter hose is used in place of the rigid optical scattering tube which, in place of the optical scattering dome, has an expandable closure cap at the distal end which is transparent to the active radiation employed and does not absorb this radiation.

A bio-compatible scattering fluid, for example a fat/oil-water emulsion, then also again flows—in the manner of an infusion solution—through this catheter hose closed off in this manner (as in the above cited example of the rigid scattering tube). Inside the catheter the laser beam is guided through a regular optical fiber, wherein the optical fiber sends the radiation into the expandable closure cap at the end of the catheter hose.

In this case the closure cap preferably has a fill volume of typically 0.5 to 2 $cm^3$—depending on the model—and in the expanded state has a length of typically 5 to 2 mm, which is also adapted to the intended field of employment. Correspondingly, the diameter in the expanded state can vary between the diameter of the catheter hose and approximately 1 cm. In this case the closure cap itself is made of a shape-retentive, only limitedly elastic plastic material in order to assume a radially-symmetrical configuration in the expanded state. The expansion state of the closure cap is controlled by means of a pressure control at the inlet side of the cooling and scattering fluid. Because of the option of expanding the distal end area, the cooled close-in area is increased and in this way the danger of local overheating is additionally counteracted. With the complementary use of a cooling thermostat in the inlet circuit of the scattering fluid it is possible to achieve an additional cooling effect at the wall of the closure cap towards the tissue via a temperature sensor in the inlet and outlet, because of which an additional protection of the tissue layers at the edge in the course of irradiation is achieved.

When using such a catheter system in the tissue, application under a compression pressure can clearly improve light dissipation in the tissues. When employing such a system in areas of the body well supplied with blood, such as the vascular system or the parenchymatous organs, it has been shown that surface cooling of the expanded closure cap by pre-cooling the scattering medium cannot assuredly prevent occasional adhesion of tissue compartments on the unfoldable plastic diaphragm of the closure cap. This problem is solved by the invention in that the diaphragm of the closure cap contains several preformed pores in the radiating direction, through which a portion of the perfusion fluid can exit and in this way always maintains a fluid film between the plastic diaphragm and the tissue. It is therefore advantageous, as mentioned above, to employ bio-compatible scattering fluids, such as a fat/oil-water-emulsion infusion solution.

With small diameters of the working shaft in the range of 2 mm and less, the increase in viscosity caused by cooling of the scattering fluid prevents a sufficient rinsing effect and thus cooling output at the tip of the working shaft.

The basic problem has essentially been solved in another advantageous further development of the invention also in that a low-boiling fluid or a gas which can be condensed at low pressure is used as the cooling fluid in such a way that this fluid is introduced into the optical working shaft either coaxially or periaxially to the fiber conducting the laser light and that the thermodynamic characteristic numbers of the fluids are selected in such a way that the fluid spontaneously vaporizes in the form of an aerosol, and by means of this vaporization process already removes vaporization heat from the vicinity of the distal end of the optical working rod whereby a cooling effect is generated. A simultaneous activation of the laser beam then causes the complete vaporization of the aerosol, which results in a further cooling effect. It is additionally achieved that because the fluid exiting at the relaxation point of the capillaries is at the critical point, so-called critical opalescence or multiple scattering takes place at the aerosol droplets and by means of this the desired additional scattering effect is generated. Heat is very efficiently removed from the vicinity by this stepped vaporization process from fluid to aerosol to gas.

At the same time such a low-boiling fluid or condensed gas has the property to have a low viscosity even with low temperatures, possibly even below freezing. Recirculation has the further advantage that it takes place only in the gaseous state, so that even with small dimensions of an optical working shaft flow resistance is practically completely prevented while at the same time cooling efficiency is increased.

If pores are omitted at the distal end of the optical working shaft, such a system can be operated in a cycle, so that it is possible in a preferred exemplary embodiment to use fluorocarbons, Freon in particular, which is not questionable even in regard to possible environmental impact in view of the use of a closed system. However, any other low-boiling fluid, such as certain alcohols or easily condensed gases, such as ethane, butane, etc. are preferably considered as cooling and scattering media.

An expandable end of the working shaft makes possible, in addition to the photo-thermal treatment, the application of pressure, particularly in connection with vascular applications. The transparency of the tissue is increased by its expansion, so that the accessible treatment area is increased. Because pores are provided, fluid can get between the front surface of the distal end of the working shaft and the adjoining tissue, so that local overheating there is prevented.

BRIEF DESCRIPTION OF THE DRAWINGS

Other advantageous further developments of the invention are featured in the dependent claims or are represented in detail below in conjunction with the description of the preferred embodiment of the invention by means of the drawing figures. Shown are in:

FIGS. 1a to c, three advantageous embodiments of the light-scattering shaft for use with an endoscope with a cylindrically rounded scattering dome, conical or mirrored on one side, FIGS. 1d and 1e, two embodiments of the invention showing advantageous configurations of the waveguide, FIG. 2, a block diagram of a device for recirculating the cooling and light-scattering fluids, FIG. 3a, a further embodiment of the invention with a flexible optical shaft, FIG. 3b, a device corresponding to FIG. 2 for use with the embodiment of the light-scattering shaft of FIG. 3a, FIG. 4a, a further embodiment of the optical working shaft of the invention with a vaporizing fluid as the cooling and scattering fluid, FIG. 4b, a simplified variant of the embodiment corresponding to FIG. 4a, FIG. 5a, a block diagram of the basic representation of a first embodiment of an external condensation device for use with an optical working shaft corresponding to FIGS. 4a and 4b, and FIG. 5b, a variant of the exemplary embodiment of FIG. 5a.

DETAILED DESCRIPTION OF THE INVENTION

Figure 1A:
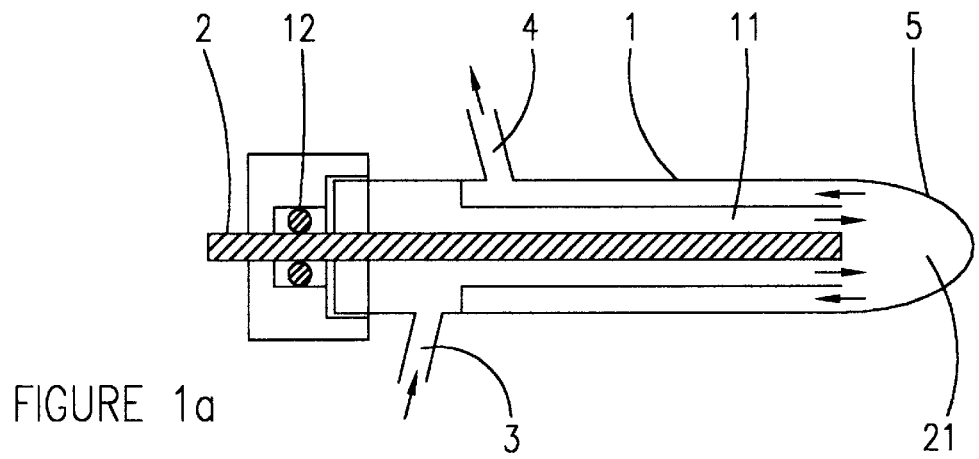
Figure 1B:
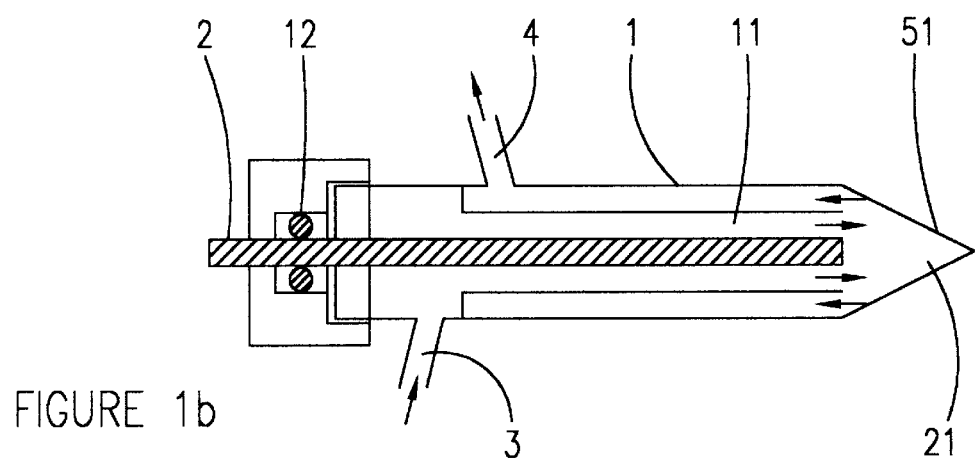
Figure 1C:
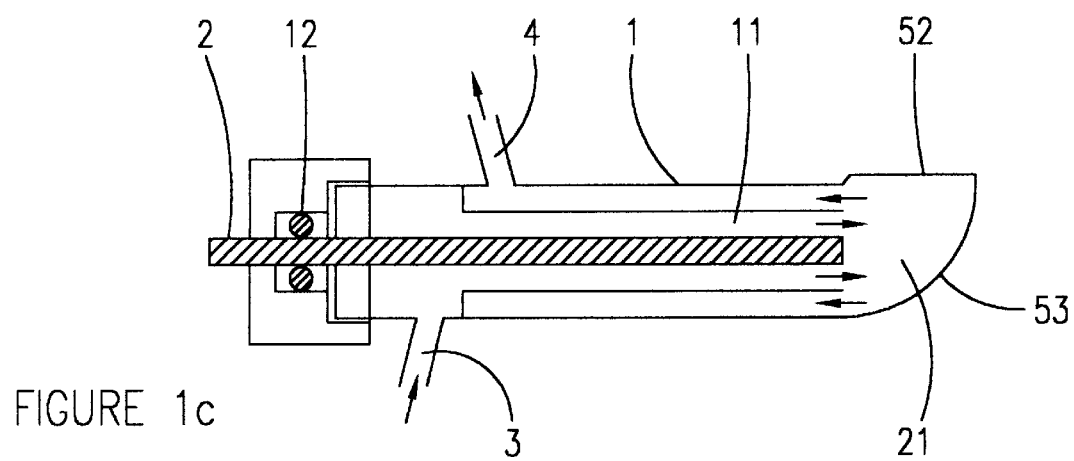

The rigid optical shaft 1 illustrated in FIGS. 1a to c can be used in this form for insertion into the working tube of an endoscope. On its distal end, the optical shaft 1 has a transparent light-scattering dome 5, into which the optical waveguide 2 is guided via an insertion lock 12. A scattering fluid 21 constituting the scattering and cooling fluid can be introduced in the direction of the arrow into the interior of the optical shaft via the inlet 3 and can recirculate in a jacket tube 11, coaxial to the outlet 4—also in the direction of the arrow In various variants of the embodiment the light-scattering dome 5 can be cylindrically rounded (FIG. 1a), conical (51 in FIG. 1b) or provided with a lateral radiating direction (FIG. 1c) created by deflection through a window 52. A mirror element 53 for the directed reflection of the active beam is provided in case of lateral radiation. It can be seen that the scattering and cooling fluid is directed from an area of the proximal end to the distal end, where it is charged with radiation via the optical waveguide 2. The fluid acts scatteringly in such a way that the beam, which at first is only directedly available at the outlet end of the optical waveguide, after being scattered by optical means—as illustrated—can be directed into the most different directions for isotropic radiation, wherein the deflection or direction selection means can be designed in the most simple manner. In the case of the embodiment in accordance with FIG. 1c, for example, a lateral spatial direction selection can take place by simply turning the working shaft together with the mirror 53 from the proximal end. The numerical aperture of the optical waveguide preferably is greater than 0.4. In particular, it is embodied as a waveguide—in an embodiment not further shown in the drawings—, so that the cooling fluid can be moved in one direction in its interior and in the other direction between the optical waveguide and the outer wall, so that no further separating wall is required.

Figure 1D:
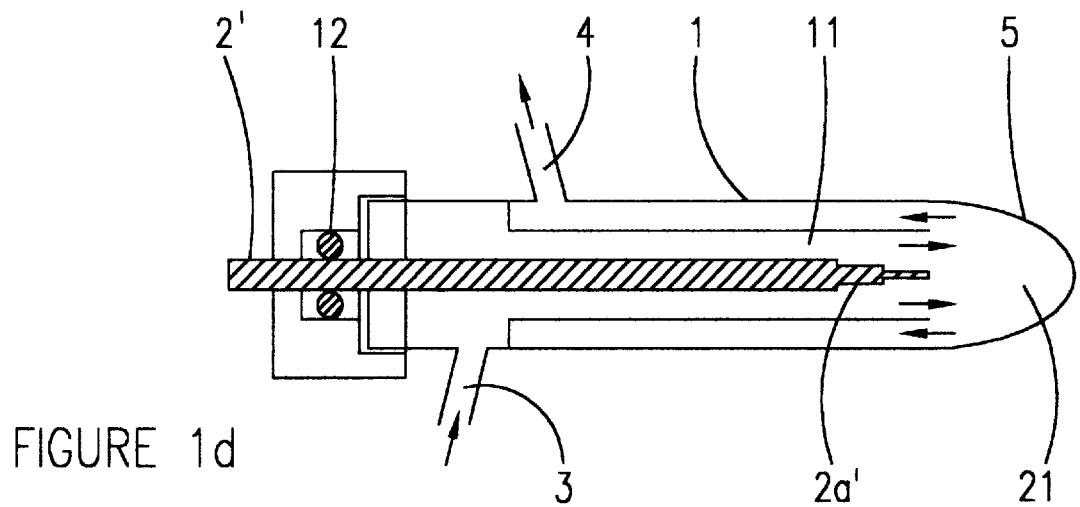
Figure 1E:
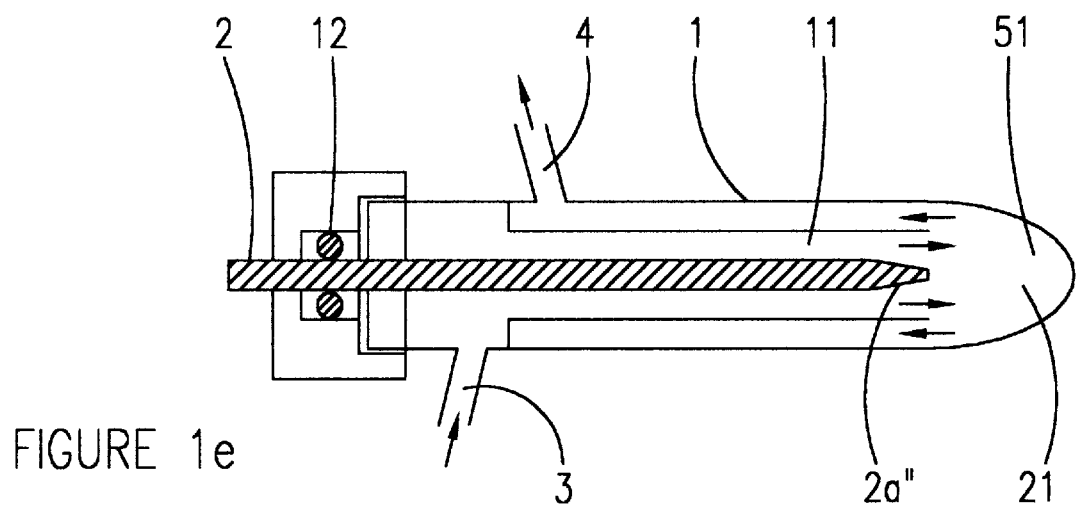

FIG. 1d shows a shaft including a waveguide 2' having a stepped distal end 2a', while FIG. 1e is a view similar to FIG. 1d showing a shaft with a waveguide 2" having a tapered distal end 2a".

Figure 2:
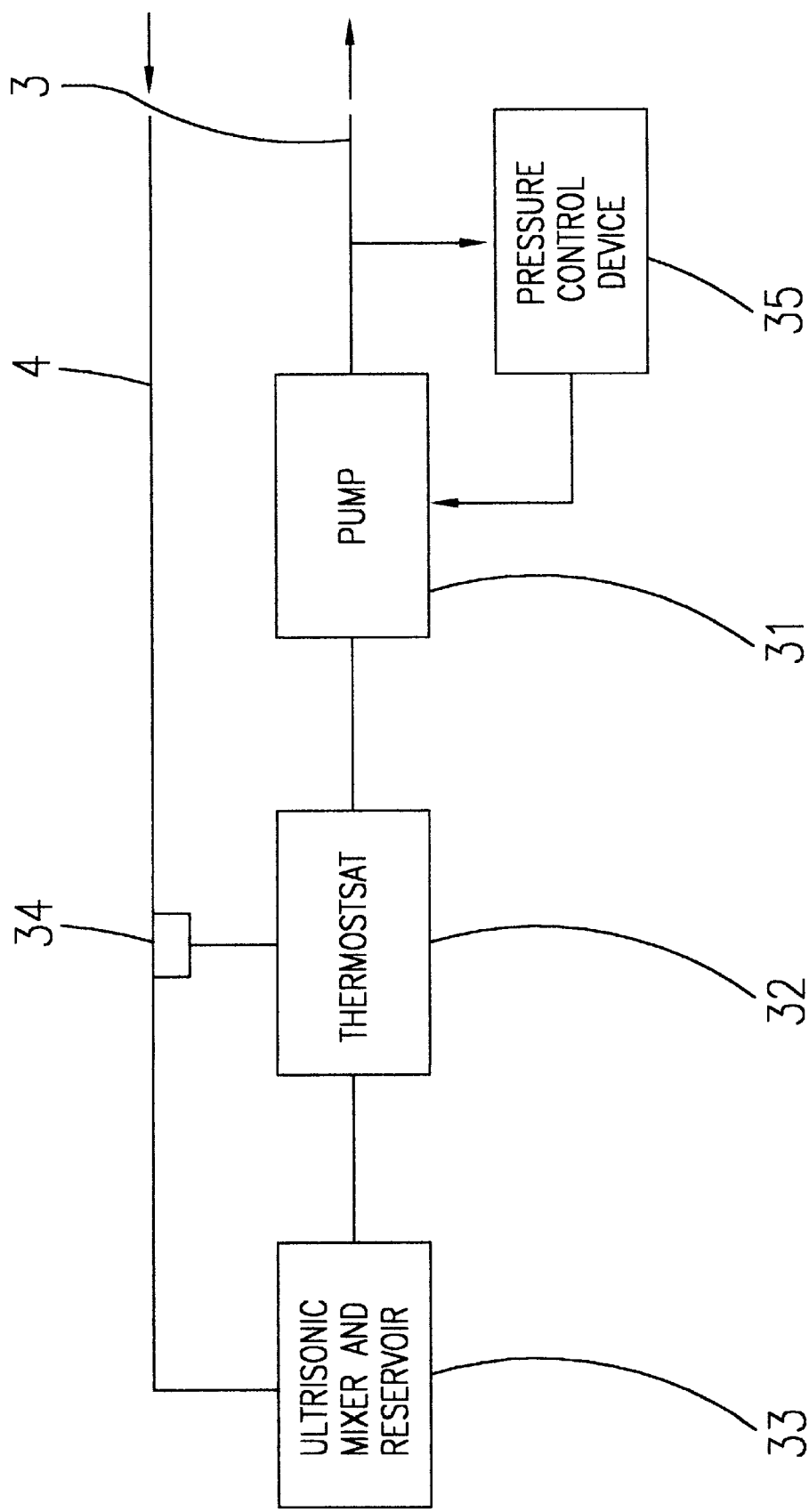

FIG. 2 shows a device for recirculating the cooling light-scattering fluid, which is homogenized in an ultrasonic mixer and reservoir 33 and is then directed via a thermostat 32, which is controlled by a temperature sensor in the return line 34, to a pump 31. The secondary pressure of the pump can be controlled via a pressure control device 35 in the inlet line 3.

Figure 3A:
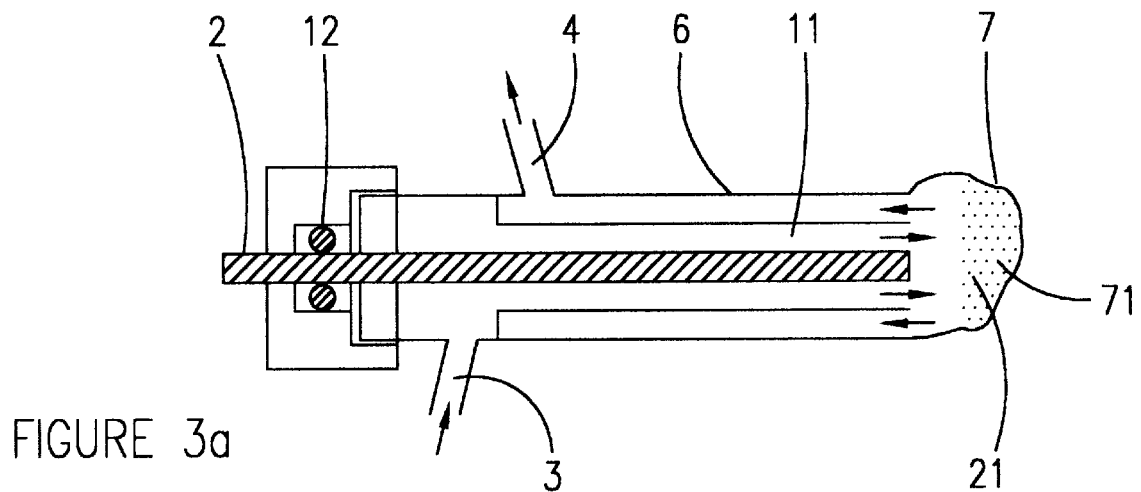

A further preferred embodiment of the invention in the form of a flexible optical shaft as the light-scattering catheter is shown in FIG. 3a. In this case a flexible catheter hose 6 is provided, which is closed off at the distal end by means of an optically transparent, partially elastic, dimensionally stable diaphragm 7, into which preformed pores 71 have been drilled. The optical waveguide 12 is again inserted into the optical shaft via a lock 12. The cooling scattering fluid 21 is introduced via an inlet 3 into the catheter with at least two hollow channels and flows via the outlet 4 to the service devices.

Figure 3B:
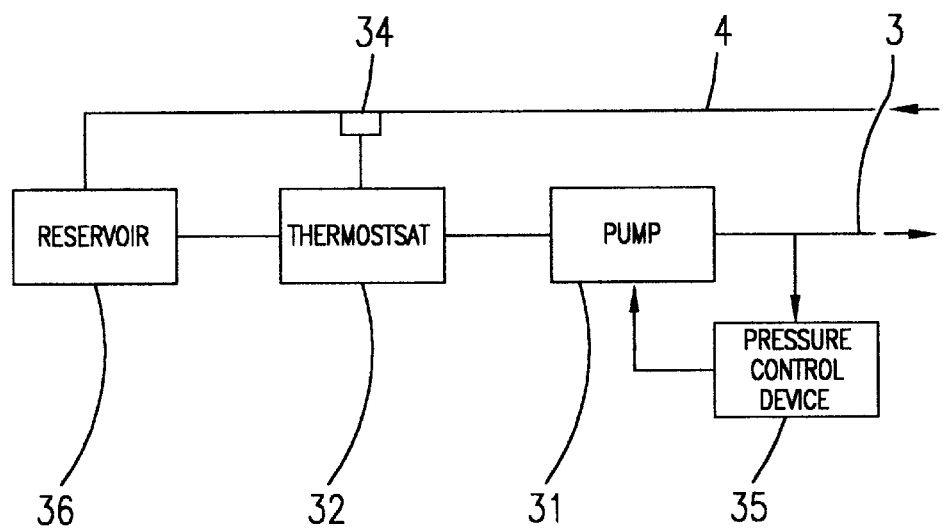

The associated service devices are individually represented in FIG. 3b. In this case the run-off is first directed to a reservoir 36, is from there carried via a thermostat 32, which is controlled by means of a temperature sensor 34 in the return line, to a pressure pump 31, which in turn is controlled via a pressure control device 35 in the inlet 3.

Figure 4A:
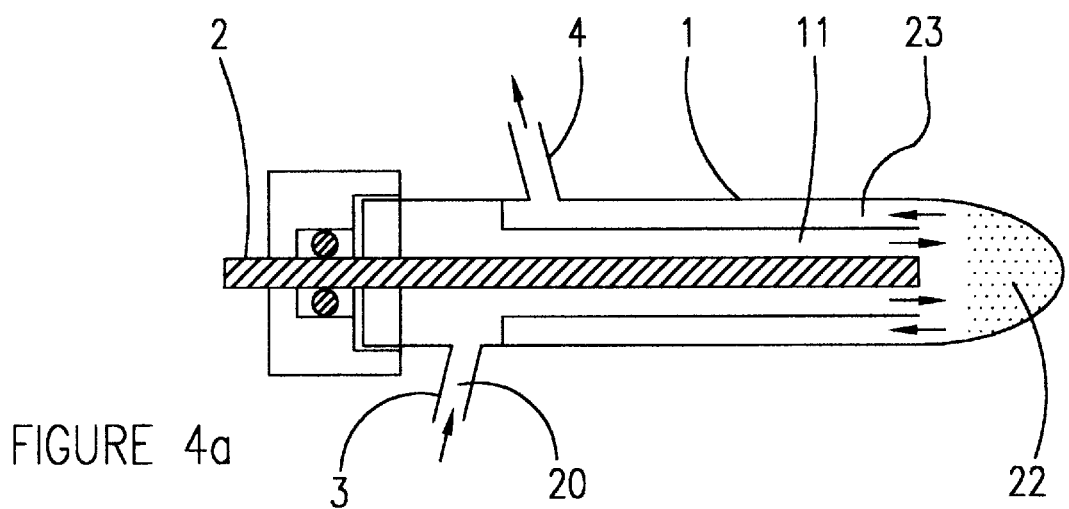

FIG. 4a shows a further disposition of the optical working shaft, in which the fluid to be vaporized is introduced, coaxially to the laser-light-transmitting optical fiber 2 in a coaxial jacket body 11, into the distal end of the optical working shaft 1 and, because of the ambient or radiation-induced temperature at the distal end, is first vaporized into an aerosol 22. During the application process the aerosol 22 vaporizes completely into a gas 22, which is supplied via an outlet connector to a condenser and is again supplied as a liquid to the process via an inlet connector.

Figure 4B:
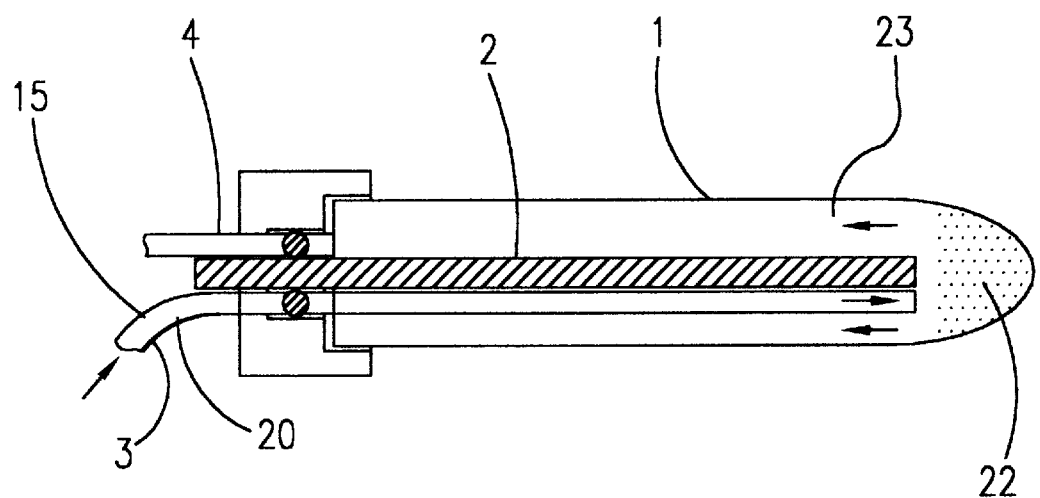

FIG. 4b shows an arrangement which is simplified in comparison with the embodiment of FIG. 4a, in which the vaporization fluid 20 is brought forward to the distal end of the optical working shaft by means of a thin hose element 15. There the aerosol and gas formation again takes place, wherein the gas 23 being generated is again supplied via an outlet connector to an external condensation device.

Figure 5A:
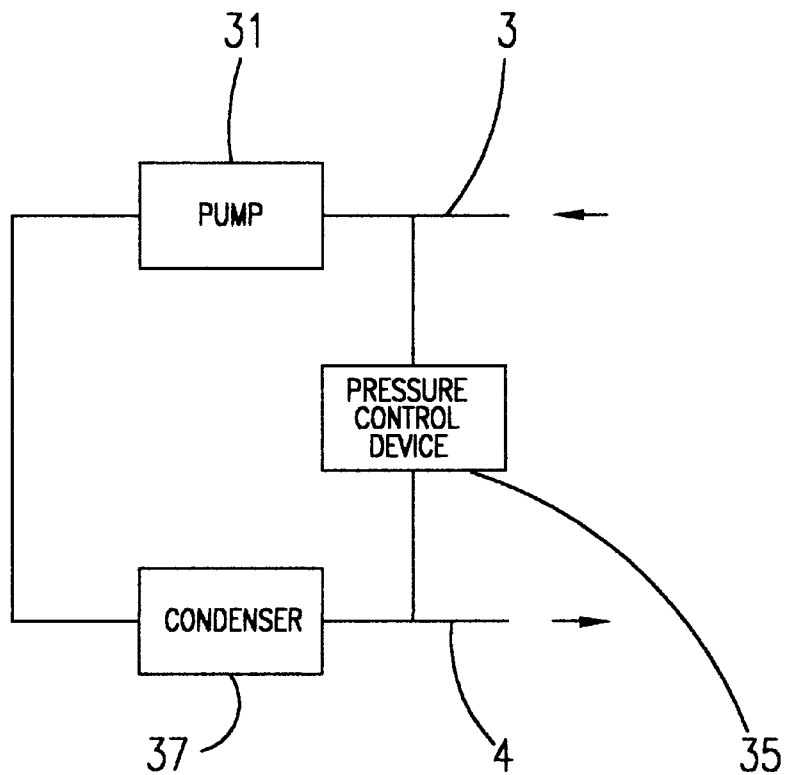

FIG. 5a shows the basic representation of an external condensation device for the case of a low-boiling fluid which can either be condensed already at room temperature or with additional cooling in a condenser 37 and is then again supplied to the process as a fluid via a pump 31. The operating point is controlled and adjusted via a pressure control device 35.

Figure 5B:
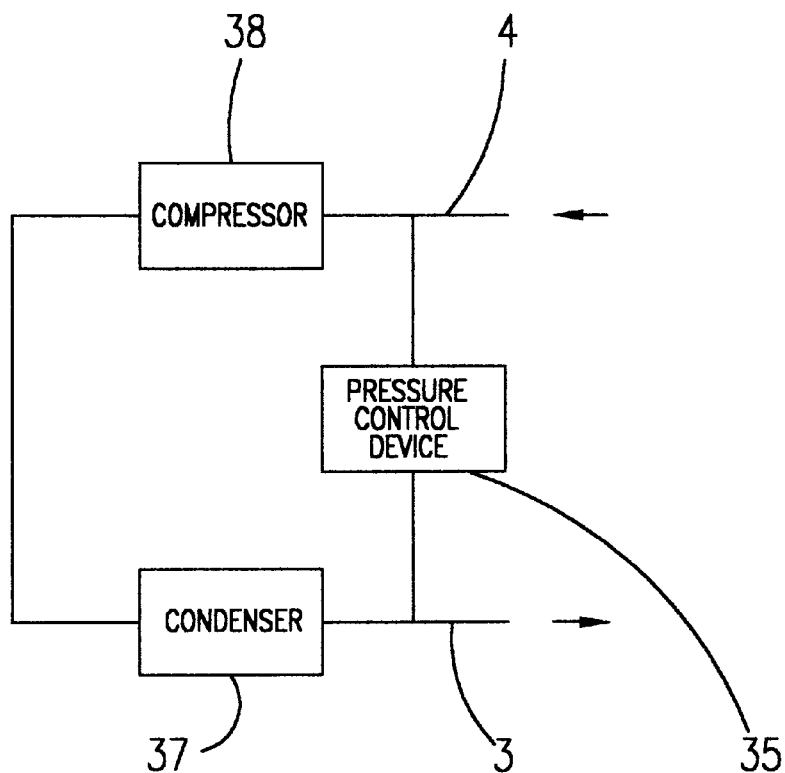

FIG. 5b shows a further exemplary embodiment of the arrangement in accordance with the invention for the case where a gas which was condensed under pressure is used as the scattering and cooling medium. In this case the gas is first compressed by means of a compressor 38 and then condensed in a condenser 37. Again, the operating point is adjusted by means of a pressure control device 35.

In a continuation of the concept of the invention, the optical waveguide 2 which guides the laser beam is embodied to taper step-wise—or in any other way—at the distal end and to have a dull surface. This can preferably be achieved by dipping the optical waveguide, from which the protective coating has been removed, into an etching fluid and then to pull it out in steps. As a result a stepped cone with a dull surface is created at the end of the optical waveguide.

As can be seen, in this case the scattering fluid adds to the non-directional distribution of the beam, which is also aided by the dulling of the surface of the transparent dome formed at the distal end. Its geometrical shape, however, represents the prerequisite for attaining a desired intensity distribution of the beam in the application area.

The use inside a body of a rigid or flexible optical shaft in accordance with the invention again can take place either by means of the working shaft of an endoscope mentioned at the outset or, during a non-endoscopic procedure, by means of a flexible catheter and the use of a trocar or a conventional lock, wherein in case of use in solid tissue it is first necessary to open the way to the location of application by means of a mandrin. Subsequently the light-scattering catheter is introduced in place of the mandrin and then the insertion instruments are pulled back far enough so that they are no longer in the actual range of the beam.

In its application the invention is not limited to the above recited preferred exemplary embodiment. Instead, a number of variants are conceivable which make use of the disclosed attainment of the object even in case of basically different designs.

We claim:

1. An optical working shaft system for photo-thermal therapy comprising a working shaft for insertion into a working tube of at least one of an endoscope and a catheter, the working shaft having a distal end defining a distal area in the vicinity thereof, the working shaft further comprising:

means for radiating, in a controlled manner, optical beams through the distal end;

an optical dome disposed at the distal end, being transparent to active components of the optical beams;

a fluid for scattering the beams contained at least in the distal end of said dome and for removing waste heat generated by a scattering of the beams, the fluid being associated with the means for radiating such that, at least in the distal area, a path of beams extends inside the fluid; and wherein said fluid for scattering and for removing waste heat has multi-phases to effect the scattering.

2. The working shaft system according to claim 1, wherein the multi-phase fluid is an emulsion of oil and water and the working shaft further comprises an ultrasonic oscillator operatively connected to the working shaft for keeping the emulsion in suspension.

3. The working shaft system according to claim 2, wherein the ultrasonic oscillator generates ultrasound for providing a dispersion thereby stabilizing the emulsion.

4. The working shaft system according to claim 1, wherein the multi-phase fluid is a liquid of a type which vaporizes readily at temperatures present in a body and its vapor.

5. The working shaft system according to claim 4, wherein the liquid is at least one of alcohol and fluorocarbon.

6. The working shaft system according to claim 4, further comprising one of a condenser pump and a compressor-condenser system for condensing a vaporized portion of the liquid thereby generating condensed fluid for supplying back into the working shaft.

7. The working shaft system according to claim 1, wherein the means for irradiating in a controlled manner comprises:

means for arriving at different concentrations of the beams by selecting a geometric design of the dome for obtaining various corresponding directional beam characteristics at the distal end.

8. The working shaft system according to claim 1, wherein the means for radiating is an optical waveguide for conveying the beams to the distal end.

9. The working shaft system according to claim 8, wherein the working shaft further includes means for conveying the fluid toward the distal end coaxially with the waveguide.

10. The working shaft system according to claim 8, wherein the waveguide has a distal end which is tapered and stepped in a direction toward the distal end of the working shaft.

11. The working shaft system according to claim 8, wherein the waveguide is a hollow waveguide.

12. The working shaft system according to claim 1, wherein the multi-phase fluid is at least one of an emulsion of silicone oil and water as coolant and optically scattering fluid, and a mixture of water with one of a fat and an oil as a bio-compatible scattering fluid and coolant.

13. The working shaft system according to claim 1, further comprises:

means for controlling a temperature of the fluid.

14. The working shaft system according to claim 1, wherein the optical dome includes preformed pores for allowing an exit of a bio-compatible fluid therethrough.

15. An optical working shaft system for photo-thermal therapy comprising a working shaft for insertion into a working tube of at least one of an endoscope and a catheter, the working shaft having a distal end defining a distal area in the vicinity thereof, the working shaft further comprising:

means for radiating optical beams through the distal end;

a fluid for scattering the beams at least in the distal area and for removing waste heat generated by a scattering of the beams, the fluid being associated with the means for radiating such that, at least in the distal area, a path of beams extends inside the fluid;

an optical dome disposed at the distal end, the dome being transparent to active components of the beams said scattering fluid being contained in at least the distal end of said dome; and wherein the dome is made from one of an opalescent mineral and glass.

16. The working shaft system according to claim 15, wherein the fluid is an emulsion of oil and water and the working shaft further comprises an ultrasonic oscillator operatively connected to the working shaft for keeping the emulsion in suspension.

17. The working shaft system according to claim 16, wherein the ultrasonic oscillator generates ultrasound for providing a dispersion thereby stabilizing the emulsion.

18. The working shaft system according to claim 15, wherein the fluid is a liquid of a type which vaporizes readily at temperatures present in a body and its vapor.

19. The working shaft system according to claim 18, wherein the liquid is at least one of alcohol and fluorocarbon.

20. The working shaft system according to claim 18, further comprising one of a condenser pump and a compressor-condenser system for condensing a vaporized portion of the liquid thereby generating condensed fluid for supplying back into the working shaft.

21. The working shaft system according to claim 15, wherein the working shaft further comprises:

means for arriving at different concentrations of the beams by selecting a geometric design of the dome for obtaining various corresponding directional beam characteristics at the distal end.

22. The working shaft system according to claim 15, wherein the means for radiating is an optical waveguide for conveying the beams to the distal end.

23. The working shaft system according to claim 22, wherein the working shaft further includes means for conveying the fluid toward the distal end coaxially with the waveguide.

24. The working shaft system according to claim 22, wherein the waveguide has a distal end which is tapered and stepped in a direction toward the distal end of the working shaft.

25. The working shaft system according to claim 22, wherein the waveguide is a hollow waveguide.

26. The working shaft system according to claim 15, wherein the fluid is at least one of an emulsion of silicone oil and water as coolant and optically scattering fluid, and a mixture of water with one of a fat and an oil as a bio-compatible scattering fluid and coolant.

27. The working shaft system according to claim 15, further comprises:

means for controlling a temperature of the fluid.

28. The working shaft system according to claim 15, wherein the optical dome includes preformed pores for allowing an exit of a bio-compatible fluid therethrough.

* * * * *